(12) United States Patent
Melsheimer

(10) Patent No.: US 7,641,844 B2
(45) Date of Patent: Jan. 5, 2010

(54) METHOD OF MAKING A FIBER-REINFORCED MEDICAL BALLOON

(75) Inventor: Jeffry S. Melsheimer, Springville, IN (US)

(73) Assignee: Cook Incorporated, Bloomington, IN (US)

( * ) Notice: Subject to any disclaimer, the term of this patent is extended or adjusted under 35 U.S.C. 154(b) by 37 days.

(21) Appl. No.: 11/953,465

(22) Filed: Dec. 10, 2007

(65) Prior Publication Data

US 2008/0157444 A1 Jul. 3, 2008

Related U.S. Application Data

(60) Provisional application No. 60/874,148, filed on Dec. 11, 2006.

(51) Int. Cl.
B29C 67/00 (2006.01)
B29C 45/00 (2006.01)
B29C 39/02 (2006.01)
A61M 29/00 (2006.01)
A61M 31/00 (2006.01)
B29C 49/00 (2006.01)

(52) U.S. Cl. .......... 264/449; 264/10; 264/314; 264/510; 264/523; 264/535; 264/454; 264/484; 264/500; 264/514; 264/465; 264/512; 604/96.01; 604/507; 604/508; 604/509; 425/535

(58) Field of Classification Search .......... 264/465, 264/500, 510, 514, 10, 314, 512, 523, 449, 264/454, 484; 428/35.9; 604/103.13, 509, 604/95.03, 96.01, 99.01; 425/535
See application file for complete search history.

(56) References Cited

U.S. PATENT DOCUMENTS

| | | | |
|---|---|---|---|
| 4,950,239 A | 8/1990 | Gahara et al. | |
| 5,587,125 A | 12/1996 | Roychowdhury | |
| 5,647,848 A | 7/1997 | Jørgensen | |
| 5,733,301 A * | 3/1998 | Forman | 606/192 |
| 6,308,509 B1 | 10/2001 | Scardino et al. | |

(Continued)

FOREIGN PATENT DOCUMENTS

| | | |
|---|---|---|
| WO | WO 2005026398 A2 * | 3/2005 |
| WO | WO 2005/037339 A1 | 4/2005 |
| WO | WO 2005037339 A1 * | 4/2005 |

OTHER PUBLICATIONS

Boland, E.D.; Wnek, G.E.; Simpson, D.G.; Pawlowski, K.J.; Bowlin, G.L. "Tailoring Tissue Engineering Scaffolds Using Electrostatic Processing Techniques: A Study of Poly(glycolic Acid) Electrospinning," *J. Macromol. Sci.*, 2001, A38(12), pp. 1231-1243.

(Continued)

*Primary Examiner*—Khanh Nguyen
*Assistant Examiner*—Vishal I Patel
(74) *Attorney, Agent, or Firm*—Brinks, Hofer, Gilson & Lione

(57) ABSTRACT

A method of making a fiber-reinforced medical balloon is described herein. The method entails pressurizing a portion of a balloon, and ejecting a fiber precursor fluid from at least one nozzle adjacent to the portion. One or more fibers are formed from the fiber precursor fluid and deposited on an exterior surface of the portion. Preferably, the fibers are polymer nanofibers, and the method is carried out using an electrospinning process.

14 Claims, 3 Drawing Sheets

U.S. PATENT DOCUMENTS

| | | | |
|---|---|---|---|
| 6,863,861 | B1 | 3/2005 | Zhang et al. |
| 6,955,658 | B2 | 10/2005 | Murray, III |
| 6,989,025 | B2 | 1/2006 | Burgmeier et al. |
| 7,037,562 | B2 | 5/2006 | Jimenez |
| 2003/0093107 | A1 | 5/2003 | Parsonage et al. |
| 2003/0143350 | A1 | 7/2003 | Jimenez |
| 2003/0229184 | A1 | 12/2003 | Acquarulo, Jr. et al. |
| 2004/0073251 | A1 | 4/2004 | Weber |
| 2004/0101644 | A1 | 5/2004 | Kinoshita et al. |
| 2004/0109964 | A1* | 6/2004 | Beckham ............... 428/35.9 |
| 2004/0138733 | A1* | 7/2004 | Weber et al. ........... 623/1.11 |
| 2005/0260355 | A1 | 11/2005 | Weber et al. |
| 2005/0261670 | A1 | 11/2005 | Weber et al. |
| 2005/0271844 | A1* | 12/2005 | Mapes et al. ........... 428/36.1 |
| 2006/0057350 | A1 | 3/2006 | Ochi et al. |
| 2007/0267128 | A1* | 11/2007 | Horn et al. ............. 156/172 |

OTHER PUBLICATIONS

Hohman, M.M.; Shin, M.; Rutledge, G.; Brenner, M.P. "Electrospinning and Electrically Forced Jets. II. Applications," *Physics of Fluids*, 2001, 13(8), pp. 2221-2236.

Rutledge, G.C.; Li, Y.; Fridrikh, S.; Warner, S.B.; Kalayci, V.E.; Patra, P. "Electrostatic Spinning and Properties of Ultrafine Fibers," *National Textile Center Annual Report*: Nov. 2001, 2001, M01-D22, pp. 1-10.

Ramakrishina, S.; Huang, Z.M.; Kotaki, M.; Lim, C.T.; Zhang, Y.Z.; Inai, R. "Electrospun Polymer Nanofibers and their Potentials," http://www.eng.nus.edu.sg/EResnews/0302/sf/sf_3.html, 2 pages.

Saab, M.A.; "Applications of High-Pressure Balloons in the Medical Device Industry," *Medical Device & Diagnostic Industry Magazine*, Sep. 2000, pp. 86-94.

Sauerteig, K.; Giese, M. "The Effect of Extrusion and Blow Molding Parameters on Angioplasty Balloon Production," *Medical Plastics and Biomaterials Magazine*, May 1998, pp. 46-52.

"Composites 1," Materials Engineering Institute, *American Society for Metals*, Materials Park, OH, 1984, pp. 7-2, 10-6, 10-7, and 10-16.

"Electrospinning," www.che.vt.edu/Wilkes/electrospinning/electrspinning.html, pp. 1-9.

\* cited by examiner

METHOD OF MAKING A FIBER-REINFORCED MEDICAL BALLOON

RELATED APPLICATIONS

The present patent document claims the benefit of the filing date under 35 U.S.C. §119(e) of Provisional U.S. Patent Application Ser. No. 60/874,148, filed Dec. 11, 2006, which is hereby incorporated by reference.

TECHNICAL FIELD

This disclosure relates generally to a method of making a medical device, and more particularly to a method of fabricating a fiber-reinforced medical balloon.

BACKGROUND

Balloon angioplasty is a widely used procedure for expanding constricted body passageways, such as arteries and other blood vessels. In an angioplasty procedure, an uninflated angioplasty balloon attached to a catheter is delivered to a constricted region of a body passageway. Once the balloon is in position at the constricted region, fluid is injected through a lumen of the catheter and into the balloon. The balloon consequently inflates and exerts pressure against the constricted region to expand the passageway. After use, the balloon is collapsed, and the catheter is withdrawn.

Balloons have a number of critical design parameters. One is rated burst pressure, which is the statistically-determined maximum pressure to which a balloon may be inflated without rupturing. In order to expand hard, calcified lesions, it is desirable that the balloon have a rated burst pressure of at least 15 bar. It is also desirable that the balloon have a low wall thickness to minimize the profile of the delivery system. A wall thickness of about 0.03 millimeters or lower is generally preferred. For a given balloon material, however, there is a trade-off between burst pressure and wall thickness, in that the burst pressure generally decreases when the wall thickness is reduced.

Accordingly, there is a need for a means of increasing the strength of balloon materials to attain higher rated burst pressures at lower wall thicknesses.

BRIEF SUMMARY

Described herein is a method of making a fiber-reinforced medical balloon. The method may provide a high-strength, thin-walled medical balloon that can withstand high inflation pressures without rupturing.

According to one aspect, the method includes pressurizing a portion of a balloon and ejecting a fiber precursor fluid from at least one nozzle disposed adjacent to the portion of the balloon. One or more fibers are formed from the fiber precursor fluid and deposited onto an exterior surface of the portion of the balloon.

According to another aspect, the method includes pressurizing a portion of a balloon and depositing one or more fibers onto an exterior surface of the portion by electrospinning.

DETAILED DESCRIPTION

Described herein is a method of making a fiber-reinforced medical balloon. The method may provide a high-strength, thin-walled medical balloon that can withstand high inflation pressures without rupturing.

Figure 1:
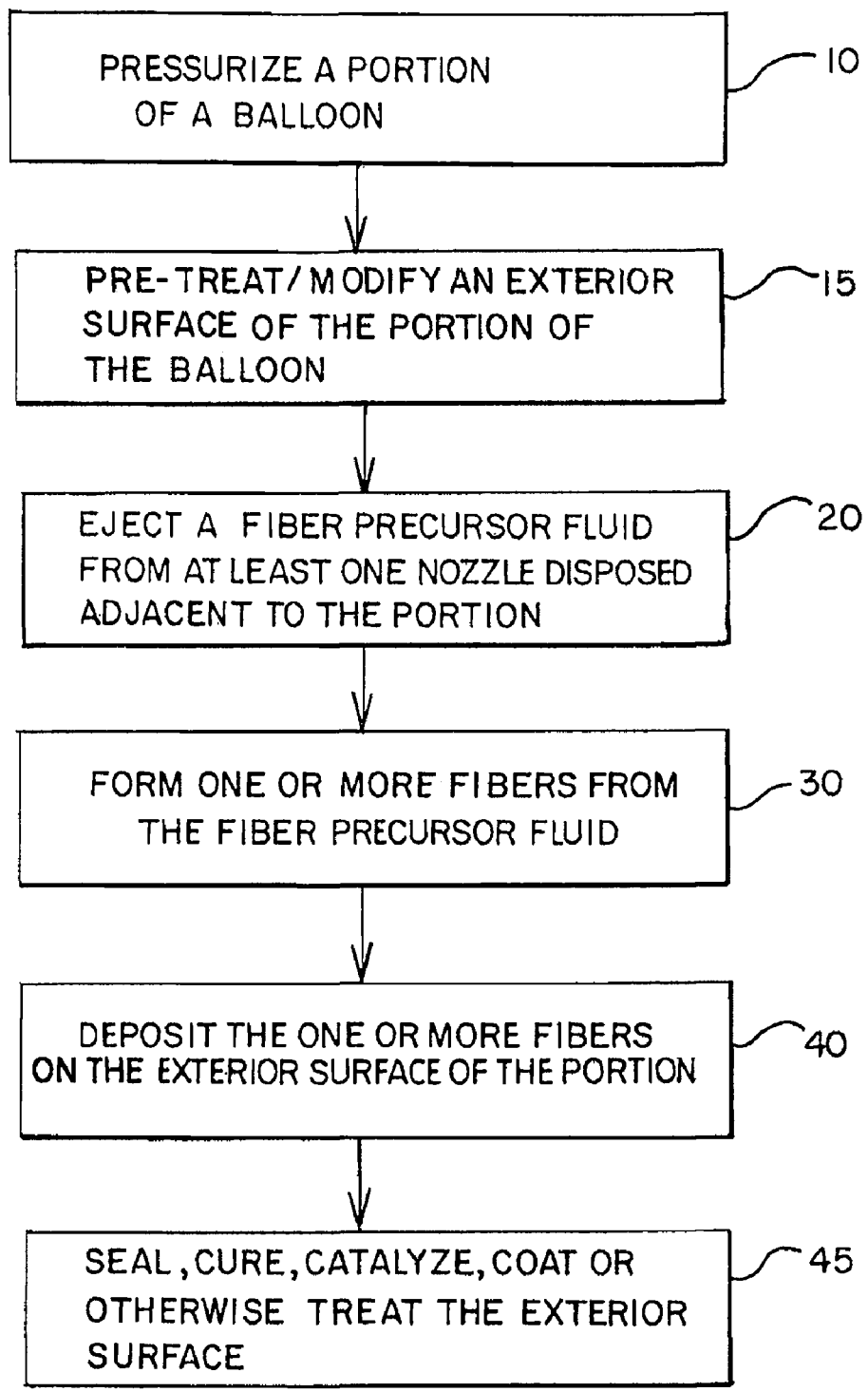
FIG. 1 is a flow diagram showing steps of the method.

Referring to the flow chart in FIG. 1, according to one aspect the method comprises pressurizing 10 a portion of a balloon, and ejecting 20 a fiber precursor fluid from at least one nozzle disposed adjacent to the portion. One or more fibers are formed 30 from the fiber precursor fluid and deposited 40 onto an exterior surface of the portion of the balloon. Prior to depositing 40 the fibers onto the exterior surface, it may be advantageous to pre-treat, prime or otherwise modify 15 the surface to aid in securing the fibers thereto. It may also be advantageous after deposition to seal, cure, catalyze, or coat 45 the exterior surface. Preferably, the fibers are polymer nanofibers. Various aspects of the process are described below.

Figure 2A:
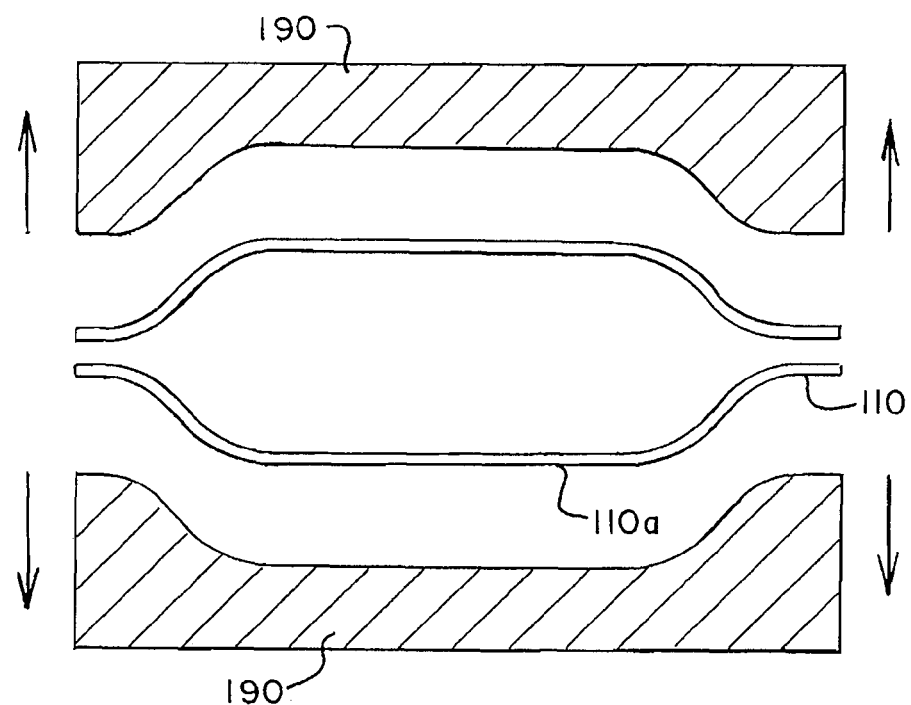
FIG. 2A is a cross-sectional schematic showing a balloon being removed from a mold after a blow molding process.
Figure 2B:
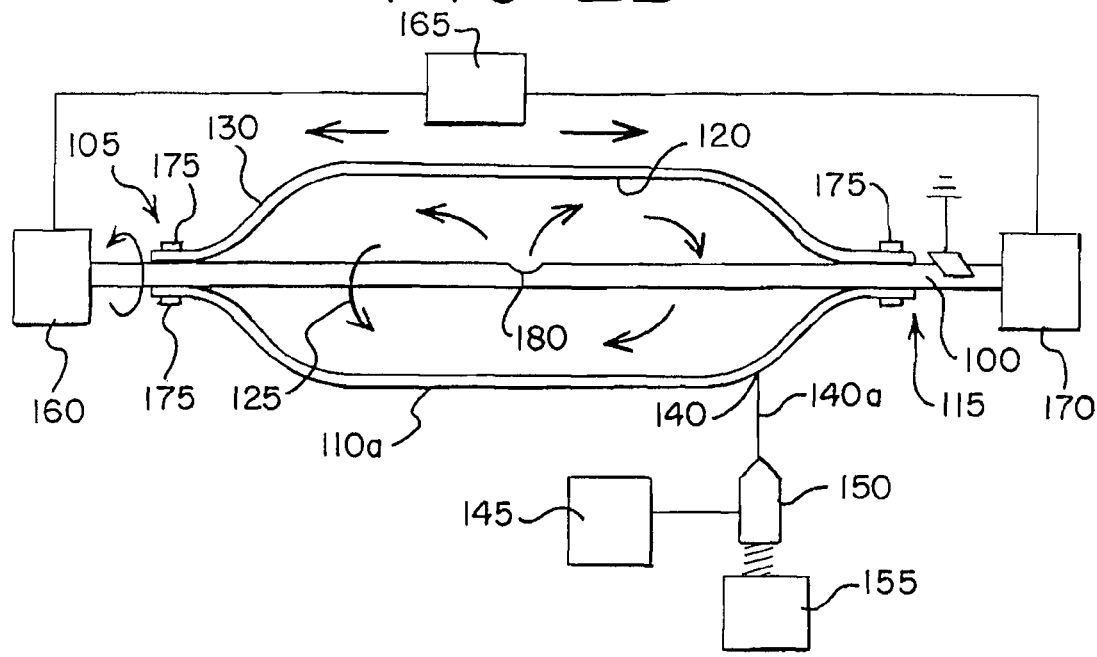
FIG. 2B is a cross-sectional schematic showing a method for depositing one or more nanofibers on an exterior surface of the balloon.

Referring to FIG. 2B, to pressurize the portion 110a of the balloon 110, the balloon 110 may be disposed over a hollow mandrel 100 having a distal end 105 and a proximal end 115 and an opening 180 therebetween in a wall of the mandrel 100. A pressurized fluid 125 may be introduced into one or both ends of the mandrel 100 from a fluid source 170. Preferably, the portion 110a is a midsection of the balloon 110. The pressurized fluid 125 travels through the mandrel 100 and out the opening 180 to exert an outward force on an interior surface 120 of the midsection 110a of the balloon 110. The fluid 125 may be a gas or liquid. For example, the pressurized fluid 125 may be compressed air. The ends 105, 115 of the balloon 110 may be sealed to the distal and proximal ends of the mandrel 100 prior to pressurizing the midsection 110a. A mechanical sealing mechanism, such as a clamp 175, may be used for sealing so that the seal is not permanent and may be released at the desired time. Alternatively, the mandrel 100 may have a nonuniform or stepped diameter that facilitates sealing one or both ends 105, 115 of the balloon 100 to the respective ends of the mandrel 100.

Depending on the compliance of the balloon material, the balloon 110 may be in an expanded state prior to introduction of the pressurized fluid 125 into the mandrel 100, or the balloon 110 may be in a deflated, collapsed configuration. Balloon materials having sufficient rigidity to maintain a given size and shape regardless of the pressure of the fluid contained therein are generally referred to as non-compliant materials, and balloon materials that appreciably elastically change in size and shape due to the pressure of the fluid contained therein are generally referred to as compliant materials. Substantially non-compliant balloon materials, such as, for example, polyethylene terephthalate (PET), are preferred for the present method. Other possible balloon materials are discussed below. Preferably, the portion 110a is pressurized to a level sufficient to remove any dents from a substantially non-compliant balloon material, or to a level sufficient to expand a compliant balloon material. For example, a positive pressure in the range of from about 1.5 atm to about 10 atm may be suitable for pressurizing the portion 110a.

Once the midsection 110a of the balloon 110 has been pressurized, one or more fibers 140 (e.g., nanofibers) may be deposited on and secured to the exterior surface 130 of the midsection 110a.

Referring again to FIG. 2B, an electrospinning process may be carried out to deposit the one or more fibers 140 onto the exterior surface 130. A nozzle (or spinneret) 135 may be disposed adjacent to the midsection 110a of the balloon 110 and a fiber precursor fluid 140a may be ejected from the nozzle 135, as shown in the figure. Preferably, the nozzle 135 serves as a first electrode and the mandrel 100 serves a second electrode, and the fiber precursor fluid 140a is electrically charged. Accordingly, the nozzle 135 may be connected to a voltage source 145 and the mandrel 100 may be grounded. The voltage source 145 may supply a voltage in the range of from about 5 kV to about 30 kV, or the voltage may be in the range of from about 10 kV to about 20 kV. Electrostatic charge may be introduced into the fiber precursor fluid 140a by charge induction through contact with the first electrode (nozzle 135). Once ejected from the nozzle 135, the electrically charged fiber precursor fluid 140a accelerates under the influence of the electric field and may follow an oscillatory and/or spiraling path to the exterior surface 130 of the expanded portion 110a. Electrospinning is described further in M. M. Hohman et al., "Electrospinning and Electrically Forced Jets. II. Applications," *Physics of Fluids,* 13, 8, Aug. 2001, 2221-2236, and in G. C. Rutledge, et al., "Electrostatic Spinning and Properties of Ultrafine Fibers," *National Textile Center, Annual Report,* November 2001, which are hereby incorporated by reference. The charged fiber precursor fluid 140a is generally ejected from the nozzle 135 in the form of a stream. Alternatively, the charged fluid 140a may be ejected in the form of a spray.

The fiber precursor fluid 140a includes a polymer and a solvent liquid, according to one aspect. Preferably, the fiber precursor fluid 140a has a polymer concentration in the range of from about 10 wt. % to about 30 wt. %. Upon ejection from the nozzle, the solvent liquid gradually evaporates from the charged fluid, leaving one or more polymeric fibers 140 that accumulate on the exterior surface 130 of the midsection 110a of the balloon 110. According to another aspect, the fiber precursor fluid 140a includes a molten polymer that thins and solidifies into one or more polymer fibers 140 after ejection from the nozzle. The polymer fibers 140 accumulate on the exterior surface 130 of the portion 110a. The flow rate of the fiber precursor fluid 140a out of the nozzle 135 is preferably in the range of from about 0.01 ml/min to about 3 ml/min, although other flow rates are possible.

The fiber precursor fluid 140a may be delivered into the nozzle 135 by a syringe-like pump 150 connected to a metering control 155 capable of controlling the flow rate of the fluid 140a. The nozzle 135 may be disposed from about 7.5 cm to about 25 cm from the exterior surface 130 during the ejection of the fiber precursor fluid 140a. Preferably, the nozzle 135 is disposed about 15 cm from the exterior surface 130. After ejection of the charged fiber precursor fluid 140a from the nozzle 135, the one or more fibers 140 are continuously or nearly continuously deposited on the exterior surface 130 of the midsection 110a. The distance of the nozzle 135 from the exterior surface 130 may affect the diameter of the one or more fibers 140 deposited on the surface 130, where the diameter generally goes down as the distance is increased.

Due to the acceleration of the fluid 140a and depending on the compliance of the midsection 110a, the one or more fibers 140 may be partially or completely embedded into the exterior surface 130 upon impact. Embedding the fibers 140 into the exterior surface 130 is discussed in further detail below.

The nozzle 135 may be configured to translate in any desired direction during the ejection and deposition process. The mandrel 100 may also be configured to translate and/or rotate. A translation control 165 and a rotation control 160 of the mandrel 100 are shown schematically in FIG. 2. Alternatively, the nozzle 135 and/or the mandrel 100 may be held stationary during the ejection of the fluid 140a and deposition of the fibers 140. By controlling the relative motion of the nozzle 135 and the mandrel 100 during the electrospinning process, it may be possible to control the positioning of the one or more fibers 140 on the exterior surface 130 of the portion 110a. For example, the mandrel 100 may rotate continuously while the nozzle 135 translates back and forth to deposit one or more fibers 140 in a helical arrangement (helical winding) on the exterior surface 130 of the expanded portion 110a. Alternatively, the mandrel 100 may remain stationary while the nozzle 135 moves about the longitudinal axis to deposit one or more fibers 140 in a pattern known as a single circuit planar or polar wrap (planar winding).

According to one aspect, more than one nozzle 135 may be used for deposition of the one or more fibers 140. For example, two or more nozzles 135 may be employed. The two or more nozzles 135 may be configured to deposit two or more nanofibers 140 in an overlapping arrangement. For example, multiple nozzles 135 may be configured to deposit fibers on the exterior surface 130 in an over-and-under pattern to obtain a braid, mesh, or other woven pattern. Alternatively, the two or more nozzles 135 may be disposed such that the nanofibers 140 are deposited separately on the exterior surface 130. For example, the fibers 140 may be deposited on the exterior surface 130 in a non-overlapping arrangement (e.g., a linear array). The arrangement of the fibers 140 may be ordered (regular) or random.

Figure 3:
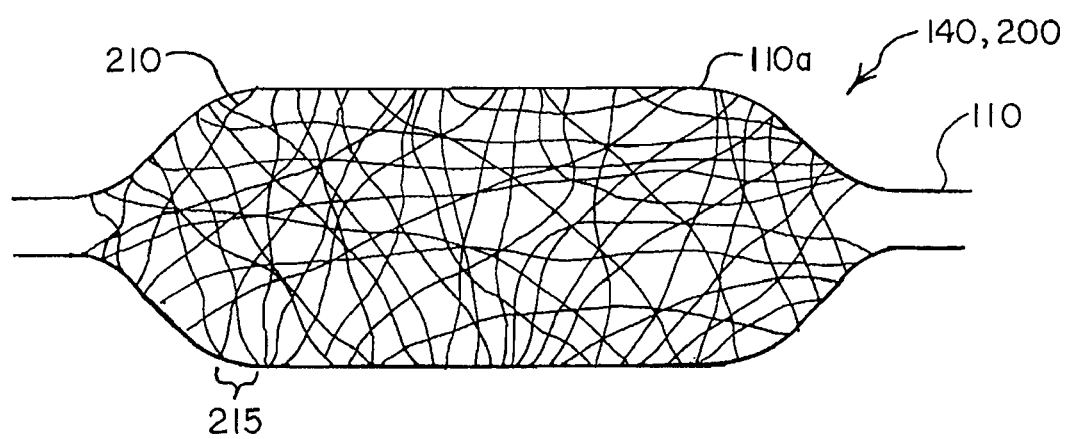
FIG. 3 is a schematic showing an exemplary random arrangement of nanofibers deposited on the exterior surface.
Figure 4:
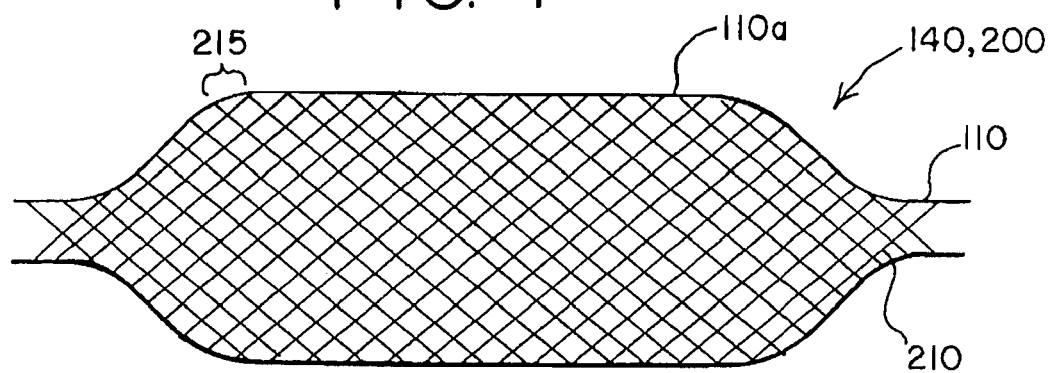
FIG. 4 is a schematic showing an exemplary ordered arrangement of nanofibers deposited on the exterior surface.

FIGS. 3 and 4 show schematically the one or more fibers 140 formed into a fiber web 200. The figures are not to scale. The web 200 may include fiber segments 210 and spacings 215 between the fiber segments 210, and may have any of the arrangements or patterns described above. The fiber segments 210 are formed by the intersection or crossing of one or more fibers 140. FIG. 3 shows an exemplary web 200 including a random arrangement of one or more fibers 140. FIG. 4 shows an exemplary web 200 including an ordered arrangement of one or more fibers 140. In some cases, it may be desirable to minimize the spacings 215 between fiber segments 210 to increase the density of fibers 140 on the exterior surface 130. As with the arrangement of fibers 140, the spacings 215 between fiber segments 210 may be controlled by adjusting the relative positioning of the nozzles 135 and the motion of the nozzles 135 with respect to each other, if more than one nozzle is employed, and also by controlling the motion of the mandrel 100 with respect to the nozzle(s).

The one or more fibers 140 deposited on the exterior surface 130 of the balloon 110 are preferably secured to the exterior surface 130. The exterior surface 130 may be pretreated, primed or otherwise modified to secure the fibers 140 thereto. The securing may entail adhering the fibers 140 to the exterior surface 130 and/or embedding the fibers 140 into the exterior surface 130. To adhere the fibers 140 to the exterior surface 130, an adhesive may be applied thereto prior to depositing the one or more fibers 140. For example, a UV light-cured cyanoacrylate adhesive such as Loctite 4306 may be employed.

To embed the fibers 140 into the exterior surface 130 of the balloon 110, which is preferably made of a thermoplastic polymer, as discussed below, the exterior surface 130 may be heated above a glass transition temperature of the polymer prior to deposition of the fibers 140. The heating may continue during deposition of the fibers 140. Above the glass transition temperature of the polymer, the polymer becomes more compliant and softens, such that the fibers 140 may become partially or fully embedded into the exterior surface 130 as they deposit thereon. Once the deposition is complete, the exterior surface 130 may be cooled below the glass transition temperature to harden, or become less compliant, and consequently secure the embedded fibers 140 in place. The heating may be carried out by exposing the exterior surface 130 to, for example, microwave energy, infrared energy, radiofrequency energy, or another heat source. The cooling may entail removing the heat source after depositing the one or more fibers 140.

Another approach to partially or fully embedding the fibers 140 into the exterior surface 130 entails applying a solvent to the exterior surface 130 prior to depositing the one or more fibers 140 as a means of softening the surface 130. The solvent may be sprayed onto the surface 130 or applied by another convenient means. The solvent may be reapplied during deposition, or continuously applied during deposition, to maintain a softened exterior surface 130. The solvent may be the solvent liquid used when creating the fiber precursor fluid, which has been entrained into the spray jet, and is thus transferred to the surface of the balloon. When the fibers 140 are deposited on the softened exterior surface 130, they may become partially or fully embedded therein. Upon evaporation of the solvent and return of the exterior surface 130 to a less compliant state, the deposited fibers 140 may be secured in place. Appropriate solvents may include, for example, acetone, methyl ethyl ketone, or methyl ethyl ketone peroxide.

Accordingly, the one or more fibers 140 deposited on the surface 130 may become an integral part of the balloon 110.

Referring to FIG. 2A, the method may further include, prior to the pressurizing step, expanding a midsection of a polymer preform in a heated mold 190 to form an expanded portion 110a of a predetermined size and shape. After forming, the expanded portion 110a may be cooled and then the mold 190 may be removed. The ends of the preform may be trimmed as desired to obtain a balloon 110, which may be further formed into a fiber-reinforced medical balloon in-line according to the above described process.

The fibers 140 (i.e., continuous fibers and fiber segments) deposited on the exterior surface 130 are characterized by a high aspect ratio. In other words, the length of a fiber is substantially larger than its diameter. Preferably, the fibers are nanofibers. The nanofibers may have a diameter in the range of from about 0.1 nm to about 10,000 nm (10 microns). For example, the diameter of the nanofibers may be about 0.1 nm or greater, about 1 nm or greater, about 10 nm or greater, or about 100 nm or greater. The diameter may also be about 10 microns (10,000 nm) or less, about 5 microns (5,000 nm) or less, about 1 micron (1,000 nm) or less, or about 0.8 micron (800 nm) or less. According to one aspect, the nanofibers may have a diameter in the range of from about 1 nm (0.001 micron) to about 5,000 nm (5 microns). An advantage of the electrospinning process is its capability of synthesizing submicron-scale polymer fibers. Accordingly, it may be desirable that the diameter of the nanofibers range from about 10 nm (0.01 micron) to about 1,000 nm (1 micron). It may also be desirable that the diameter of the nanofibers range from about 100 nm (0.1 micron) to about 800 nm (0.8 micron). Alternatively, the fibers deposited on the interior surface 130 of the expanded balloon portion 110a may be greater than 10 microns in diameter.

The spacing between the fiber segments may range from a few nanometers to several hundred microns. For example, the spacing between segments may be, on average, about 10 nm or greater, about 100 nm or greater, about 1,000 nm (1 micron) or greater, or about 10,000 nm (10 microns) or greater. The spacing between segments may also be, on average, about 1,000 microns or less, about 800 microns or less, about 500 microns or less, about 100 microns or less, or about 10 microns or less. Accordingly, the spacing between the fiber segments may range from about 10 nm (0.01 micron) to about 1,000 microns. Preferably, the spacing between the fiber segments is in the range of from about 10 microns to about 1,000 microns.

The fibers may be made of one or more natural or synthetic materials. Preferably, the materials are biocompatible. According to one aspect, the fibers are made of at least one polymer. The polymer may be selected from the group consisting of poly(ε-caprolactone) (PCL), poly(lactic acid) (PLA), poly(glycolic acid) (PGA), poly(lactide-co-glycolide) (PLGA), poly(L-lactide) (PLL), poly(L-lactide-co-ε-caprolactone) [P(LLA-CL)], polyurethane (PU), polyethylene oxide (PEO), polyethylene terephthalate (PET), poly (ester urethane)urea (PEUW), poly[bis(p-methylphenoxy) phosphazene] (PNmPh), poly(p-dioxanone-co-L-lactide-block-poly(ethylene glycol) (PPDO/PLLA-b-PEG), and polyamides. Preferred natural materials include collagen, gelatin (denatured collagen), elastin, alpha-elastin, tropoelastin, and chitosan.

The balloon 110 may be made of one or more suitable biocompatible polymers. Preferably, the polymer is a thermoplastic polymer. For example, the polymer may be a polyester, including polyethylene terephthalate (PET), polybutylene terephthalate (PBT), polyethylene naphthalate (PEN), and ethylene terephthalate copolymers; polyamide, including nylon 11 and nylon 12; polyurethane; polyethylene; polyvinyl chloride; polycarbonate; poly(meth)acrylate; maleate; polyether etherketone (PEEK); poly(ethylene-co-methacrylic acid) (EMAA); polyamide/polyether block copolymer, polyester/polyether block copolymer; polyamide/polyether polyester copolymer (e.g., Pebax®); or PBT-polybutylene oxide block copolymer.

Preferably, the balloon 110 is formed by extrusion and blow molding methods known in the art to have an expanded midsection. After forming, the wall of the expanded midsection preferably has a thickness in the range of from about 0.005 mm to about 0.025 mm. The fiber web may not substantially increase the wall thickness of the expanded midsection due to the generally submicron-scale diameter of the fibers. For example, a nanofiber of 100 nm (nanometers) in diameter equates to a thickness of 0.0001 mm (millimeter). The fiber web may include multiple layers of nanofibers or overlapping nanofibers.

The presence of one or more fibers, preferably nanofibers, may improve the strength and burst pressure of the medical balloon. Preferably, the medical balloon formed by the process described herein achieves a rated burst pressure of at least 15 bar. The rated burst pressure (RBP) is the statistically-determined maximum pressure to which a balloon may be inflated without rupturing. Normally, there is a 95% confidence that 99.9% of the balloons will not burst at or below the RBP upon single inflation. The medical balloon may also achieve a rated burst pressure of at least 20 bar. It is further desirable that the medical balloon may achieve a rated burst pressure of at least 25 bar, or at least 30 bar.

The presence of the fibers or nanofibers may also facilitate drug delivery during balloon angioplasty or other medical procedures. Drug compounds or other pharmaceutical agents may be included in the fiber precursor fluid, according to one aspect of the method. For example, one or more pharmaceutical agents may be bound to the polymer in the fiber precursor fluid before the fluid is electrospun. Consequently, the fibers formed from the fluid and deposited on the exterior surface of the expanded balloon portion may include one or more therapeutically active substances. Preferably, the fibers including the therapeutically active substance(s) are embedded into the wall of the balloon. The therapeutically active substance may be able to diffuse through the exterior surface of the balloon to reach a treatment site.

A method of making a fiber-reinforced medical balloon has been described. The method entails pressurizing a portion of a balloon, and ejecting a fiber precursor fluid from at least one nozzle adjacent to the portion. One or more fibers are formed from the fiber precursor fluid and deposited on an exterior surface of the portion. Preferably, the fibers are polymer nanofibers, and the method is carried out using an electrospinning process. The method may provide a high-strength, thin-walled medical balloon that can withstand high burst pressures. The method may also provide a medical balloon with drug delivery capabilities.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A method of making a fiber-reinforced medical balloon, the method comprising:
    disposing a balloon over a hollow mandrel, the mandrel having a distal end and a proximal end and an opening therebetween in a wall of the mandrel;
    introducing a pressurized fluid into the mandrel, the fluid traveling through the mandrel and out the opening to exert an outward force on an interior surface of a portion of the balloon, thereby pressurizing the balloon;
    ejecting an electrically charged fiber precursor fluid from at least one nozzle disposed adjacent to the portion of the balloon, the nozzle comprising a first electrode and the mandrel comprising a second electrode;
    forming one or more fibers from the electrically charged fiber precursor fluid;
    depositing the one or more fibers onto an exterior surface of the portion of the balloon while the balloon is pressurized.

2. The method of claim 1, wherein the fibers are nanofibers having a diameter in the range of from about 0.1 nm to about 10 microns.

3. The method of claim 1, wherein the balloon is formed of a polymer that is substantially non-compliant.

4. The method of claim 1, wherein the mandrel is rotatable and translatable.

5. The method of claim 1, wherein the nozzle is translatable.

6. The method of claim 1, comprising two or more nozzles.

7. The method of claim 1, wherein the fiber precursor fluid is ejected from the nozzle as a stream of fluid and includes at least one of a polymer in a solvent liquid and a molten polymer.

8. The method of claim 7, wherein forming the one or more fibers from the fiber precursor fluid includes at least one of evaporation of the solvent liquid and solidification of the molten polymer.

9. The method of claim 1, wherein the one or more fibers are deposited on the exterior surface of the portion in an ordered arrangement.

10. The method of claim 1, wherein depositing the one or more fibers on the exterior surface of the portion comprises at least one of embedding the fibers into the exterior surface and adhering the fibers to the exterior surface.

11. The method of claim 10, wherein embedding the one or more fibers into the exterior surface comprises one of heating the surface and applying a solvent to the surface.

12. The method of claim 1, further comprising, prior to disposing the balloon over the hollow mandrel, expanding a midsection of a polymer preform in a mold to obtain an expanded portion of a predetermined size and shape, and then removing the mold, thereby forming the balloon.

13. The method of claim 1, wherein the fibers are nanofibers having a diameter in the range of from about 0.1 nm to about 10 microns and the balloon is formed of a polymer that is substantially non-compliant, and
    wherein the mandrel is rotatable and translatable.

14. The method of claim 13, wherein the fiber precursor fluid is ejected from the nozzle as a stream of fluid, the fiber precursor fluid including a polymer in a solvent liquid,
    wherein forming the one or more fibers from the fiber precursor fluid includes evaporation of the solvent liquid,
    wherein the fibers are deposited in an ordered arrangement, and
    wherein depositing the one or more fibers on the exterior surface of the portion comprises embedding the one or more fibers into the exterior surface, the fibers thereby becoming an integral part of the portion.

* * * * *